United States Patent [19]

Lapidus

[11] Patent Number: 4,844,712

[45] Date of Patent: Jul. 4, 1989

[54] DYEING COMPOSITION FOR FIBROUS MATERIALS

[75] Inventor: Herbert Lapidus, Ridgefield, Conn.

[73] Assignee: Combe Incorporated, White Plains, N.Y.

[21] Appl. No.: 607,722

[22] Filed: May 7, 1984

Related U.S. Application Data

[63] Continuation of Ser. No. 37,547, May 11, 1989, abandoned, Continuation-in-part of Ser. No. 951,998, Oct. 20, 1978, abandoned.

[51] Int. Cl.$^4$ .................................................. A61K 7/13
[52] U.S. Cl. .................................................. 8/435; 8/405; 8/414; 8/416; 8/604
[58] Field of Search .................. 8/406, 415, 416, 435, 8/405, 406, 415, 416, 424, 414, 435

[56] References Cited

U.S. PATENT DOCUMENTS

| | | | |
|---|---|---|---|
| 2,089,212 | 8/1937 | Kritchevsky | 260/404 |
| 2,290,945 | 7/1942 | Dahlen et al. | 8/564 |
| 3,086,914 | 4/1963 | Soloway | 424/64 |
| 3,980,091 | 9/1976 | Dasher et al. | 132/209 |

FOREIGN PATENT DOCUMENTS

| | | |
|---|---|---|
| 477917 | 10/1976 | Australia . |
| 2624293 | 1/1978 | Fed. Rep. of Germany . |
| 96718 | 4/1973 | German Democratic Rep. . |
| 414271 | 11/1980 | Sweden . |
| 139485 | 4/1930 | Switzerland . |
| 307948 | 3/1929 | United Kingdom . |

OTHER PUBLICATIONS

J. F. Corbett in Venkataraman's "The Chemistry of Synthetic Dyes", vol. V, (Academic Press 1971), pp. 475–483, 505–506 and 508.

*Primary Examiner*—A. Lionel Clingman
*Attorney, Agent, or Firm*—Roland T. Bryan

[57] ABSTRACT

An enhancer or promoter useful for improving the dyeing of fibrous materials is described. This enhancer is N-acetyl ethanolamine. It operates to facilitate dyeing of the material so as to accelerate, deepen and/or fix the coloration imparted to the material.

8 Claims, No Drawings

DYEING COMPOSITION FOR FIBROUS MATERIALS

This application is a continuation of application Ser. No. 37,547 filed May 11, 1979, now abandoned which was a continuation-in-part of application Ser. No. 951,998 filed Oct. 20, 1978 also now abandoned.

BACKGROUND OF THE DISCLOSURE

Numerous dye systems have been employed to impart desired color to fibrous materials. These systems include dyestuffs (or dye systems) having quite distinct chemical compositions, uses and mechanisms of coloration.

A major field of dye use lies in coloration of fibrous materials. Such uses encompass literally thousands of different dyestuffs developed primarily over the past one hundred years to meet the specific requirements engendered by the wide variety of fabrics involved.

By the way of example, reference is made to the Chapter entitled "Dyes" in Kirk-Othmers' *Encyclopedia of Chemical Technology* (Interscience 1950) for a discussion of this field. There mention is made of the various fibrous materials (commonly classified as "natural"-- including cellulose-based fibers such as cotton; keratin-based fibers such as wool; and fibroin-based fibers such as silk--"man-made"-- including derivatives of natural fibers such as rayon--and "synthetic"--such as nylon, polyester and polyolefin fibers of non-natural derivation). Similarly, different types of dyestuffs useful with various of these fibers are mentioned and include: acid, basic, direct, sulfur, vat, leuco esters, azo, acetate, pigment, oxidation, natural and inorganic dyes.

In addition to this broad field of fibrous, there are allied or ancillary fields of dye application. Of these, the most important is the cosmetic industry. There, in particular, dyestuffs are utilized for coloration of hair, a keratinaceous material. In this field, still greater limits are placed upon the use of dye systems because of the need to avoid toxicity or other adverse affects on the subject's skin or hair.

While the foregoing is by no means complete, it is indicative of the long history of dyes, the variety of types of dyestuffs, mechanisms of dyeing and dye applications in this art. Despite this history, however, completely satisfactory dyeing has not always been achieved. Among the drawbacks of known dye systems are: the resistance of the dyed materials to fading; the resistance of the dyed materials to erosion of color by rubbing and the like; the degree of color imparted to the materials incident to dyeing; and/or the efficiency and ease with which dye is imparted to materials for their coloration.

Much effort has been expended in seeking improved means of dyeing fibrous materials. In general, however, the known means of facilitating and improving such dyeing processes have had only occasional and/or limited success. These means have often proven expensive, successful only for alleviation of some of the foregoing drawbacks and/or useful only with certain types of the foregoing dye systems.

DESCRIPTION OF THE INVENTION

In accordance with the present invention, it has been discovered that the incorporation of N-acetyl ethanolamine into dyeing compositions provides enhanced and more durable coloration than has heretofore been obtained. These N-acetyl ethanolamine-improved or promoted compositions facilitate dyeing by accelerating the dyeing process and/or providing dyed products of enhanced and more resistant colors.

This invention has been found to be useful throughout the breadth of different dyestuffs in this art. Of particular importance, it has wide applicability to the different types of fibrous materials. Thus, it may be utilized for the dyeing of fibrous materials such as keratin based fibers, cellulose based fibers or man-made natural or synthetic fibers and other natural or man-made fibrous materials and for the treatment of human hair.

N-acetyl ethanolamine has long been recognized in the cosmetics art as a highly efficient conditioner or grooming aid for hair. Many products including shampoos, rinses, conditioners, and the like containing various amounts of N-acetyl ethanolamine are known and commercially available. It has not, however, heretofore been appreciated that N-acetyl ethanolamine will also function to promote or enhance dyeing of hair. Neither has it been recognized that this promotion of dyeing occurs not only with hair but also with other fibrous materials or that this further property is evident not only with conventional hair dyeing compositions but also with other dye systems.

In addition to its newly discovered property or function as a dyeing enhancer, N-acetyl ethanolamine continues to provide those advantages for which it has been generlly recognized in the cosmetic art. Accordingly, its presence in a dyeing composition continues to provide the grooming or conditioning functions for which it is well known. Therefore, the present dyeing compositions, in addition to providing improved coloration, are also less harsh in their effects on the material being dyed.

Although it is not wished to be bound by any theory, it is believed that at least one of the means by which the present N-acetyl ethanolamine functions to provide enhanced or promoted dyeing is through its ability to cause fiber expansion in the material being treated. Such expansion of the individual fibers of the material being dyed could account for improved and accelerated penetration of a dye system into the material. Also, it could help to explain the observed acceleration and ease in imparting coloration and/or enhanced resistance of the dyed material to fading or loss of coloration.

As has already been indicated, the chemical composition and mechanism of the dye system utilized in the present compositions is relatively unimportant. Any of the well known systems of the prior art-including, for example, oxidative dyestuffs, basic dyes and heavy metal salt/sulfur-containing reducing compound systems such as those described above--may be utilized therein.

These dye systems of the prior art normally comprised up to about 50% and preferably from about 1% to 25% by total weight of the present dyeing composition. The exact proportions, however, vary from system to system and with their intended use in a conventional manner. They also are not critical to the function of the N-acetyl ethanolamine.

In the present dye compositions (as in the prior art), the dye system is provided in a liquid, dispersing vehicle therefor. The vehicle is commonly water or an aqueous mixture. This is not required, however, as non-aqueous systems including alcohol, mineral oil and the like may be employed. Similarly mixed aqueous/water-immiscible liquid systems such as emulsions are suitable vehicles for dye systems in the present composition.

The N-acetyl ethanolamine may be employed in almost any amount; however, it normally comprises from about 1 to 25% preferably 10 to 15%, of the total weight of the dye composition. While these proportions generally provide maximum dye promotion, still greater amounts of N-acetyl ethanolamine may be present for the additional purpose of providing conditioning and/or grooming characteristics to the treated fibrous material or where the N-acetyl ethanolamine constitutes a major part, or all, of the vehicle itself. Consequently, the amount of N-acetyl ethanolamine utilized in any given dyeing composition may vary widely in accordance with the foregoing.

While the present invention has been described largely in terms of pre-formed compositions to be applied to the material being dyed, this need not be the case. The present compositions may also be formed on the fibrous material itself, through sequential applications of N-acetyl ethanolamine and of the dye system. It is thus necessary only that all of the essential components of the present dyeing composition be present on, or in, the fibrous material being dyed at the same time. This will achieve the advantages already described hereinabove.

In order more clearly to describe this invention, several examples of compositions of the present invention are described below. It should be understood, however, that these examples are provided solely for illustration and are not intended to limit the scope of the invention.

EXAMPLE I

Aqueous dyeing compositions of two standard dyes, FD&C Blue #1 (at 0.25% by weight) and D&C Yellow #10 (at 0.75% by weight), were employed in comparative dye tests for the effects of N-acetyl ethanolamine. Paired samples of these two dyeing compositions--a control sample containing 0% and a sample containing 10% of N-acetyl ethanolamine by weight--were used for the comparision.

Swatches containing different fabric materials were immersed in the four test sample dyeing compositions under identical conditions of 60° C. for 1 minute. After drying, the swatches were visually compared for intensity of dye color. The test results showed several instances in which N-acetyl ethanolamine unexpectedly affected dyeing (not all the fabric materials are normally susceptible to these particular dye compositions), as well as others in which dyeing was clearly enhanced over the respective control samples. The fabric materials which evidenced increases in color intensity due to the presence of the N-acetyl ethanolamine ranged broadly in types of fibers and included wool and worsted wool, rayon (trade name AVRIL), viscose rayon, silk, nylon, cotton, acetate, acrylonitrile (ACRILAN), triacetate (ARNEL), acrylic (CRESLAN, ORLON and ZEFRAN), polyester (DACRON, FORTREL and KODEL), olefin (HERCULON) and modacrylic fibers (VEREL and DYNEL).

From visual inspection, swatches dyed in the presence of N-acetyl ethanolamine were also deemed more homogeneous in color and less susceptible to runs and streaking. Thus the N-acetyl ethanolamine appeared to improve the fix or set of the dye to the fabric materials.

EXAMPLE II

A dyeing composition was prepared having the following formula:
Bismuth Citrate: 0.50%
Triethanolamine: 3.00%
Alcohol: 10.00%
Sulfur, precipitated: 0.50%
Triton X-100: 0.10%
N-acetyl ethanolamine: 15.00%
Water: 70.80%
Perfume: 0.10%

The above dye composition was formed in a conventional manner with the N-acetyl ethanolamine (Acetamide MEA) being added after combination of the other ingredients. To test this composition, swatches of bleached hair were dunked into the hair dyeing composition, removed, shaken to remove excess composition, and then permitted to dry overnight at room temperature. After drying, the hair was observed to have changed from its initial blondish color to a shade of brown. Repeated daily treatments, over a one-week period, yielded an increasingly deeper or darkened shade of brown coloration of high durability.

EXAMPLE III

A dyeing composition was prepared having the following formula:
Paraphenylene diamine sulfate: 5.00%
Resorcinol: 1.00%
Alcohol: 15.00%
N-acetyl ethanolamine: 10.00%
Oleic acid: 0.40%
Ammonia (25% soln.): 10.00%
Water: 63.60%

This hair dyeing composition was prepared in conventional manner and employed with a peroxide developer. In testing on bleached swatches of hair, it produced a dark black coloration.

EXAMPLE IV

A semi-permanent dye and shampoo was prepared in accordance with the following formula:
Monoethanolamine Lauryl Sulfate: 20.00%
Ethylene Glycol Mono Stearate: 3.00%
P-Nitro-o-phenylenediamine: 1.50%
Diethanolamine coconut fatty acide: 3.00%
N-acetyl ethanolamine: 7.00%
Water: 65.50%

Used in testing by shampooing hair, an enhanced coloration with increased resistance to erosion of coloration by rubbing off was observed.

What is claimed is:

1. In a composition for dyeing a fibrous material comprising a dye system and a liquid dispersing vehicle therefor, the improvement wherein said composition contains N-acetyl ethanolamine to promote dyeing of said material and wherein the dye system comprises a heavy metal salt with a sulfur-containing reducing compound.

2. The composition of claim 1, wherein the salt comprises a complex of bismuth citrate and triethanolamine.

3. The composition of claim 2, wherein the reducing compound is sulfur.

4. In a composition for dyeing a fibrous material comprising a dye system and a liquid dispersing vehicle therefor, the improvement wherein said composition contains N-acetyl ethanolamine to promote dyeing of said material and wherein the fibrous material is hair.

5. A dyeing composition comprising the following constituents each in percentage of the total weight of said composition as follows:
   Bismuth Citrate: 0.50%
   Triethanolamine: 3.00%
   Alcohol: 10.00%
   Sulfur, precipitated: 0.50%
   Triton X-100: 0.10%
   N-acetyl ethanolamine: 15.00%
   Water: 70.80%
   Perfume: 0.10%

6. A dyeing composition comprising the following constituents each in percentage of the total weight of said composition as follows:
   Paraphenylene diamine sulfate: 5.00%
   Resorcinol: 1.00%
   Alcohol: 15.00%
   N-acetyl ethanolamine: 10.00%
   Oleic acid: 0.40%
   Ammonia (25% soln.): 10.00%
   Water: 63.60%

7. A dyeing composition comprising the following constituents each in percentage of the total weight of said composition as follows:
   Monoethanolamine Lauryl Sulfate: 20.00%
   Ethylene Glycol Mono Stearate: 3.00%
   P-Nitro-o-phenylenediamine: 1.50%
   Diethanolamine coconut fatty acide: 3.00%
   N-acetyl ethanolamine: 7.00%
   Water: 65.60%

8. The composition of claim 1, wherein the fibrous material is composed of keratinous fibers.

* * * * *